United States Patent [19]

Hickey et al.

[11] Patent Number: 6,143,805
[45] Date of Patent: Nov. 7, 2000

[54] ELECTRON BEAM STERILIZATION OF LIQUID ADHESIVE COMPOSITIONS

[75] Inventors: Timothy Hickey, Raleigh; Ubonwan A. Stewart, Durham, both of N.C.

[73] Assignee: Closure Medical Corporation, Raleigh, N.C.

[21] Appl. No.: 09/025,472

[22] Filed: Feb. 18, 1998

[51] Int. Cl.[7] .................................. C08F 2/46; C08F 2/48
[52] U.S. Cl. ........................... 522/152; 522/173; 522/77; 522/79; 522/74; 523/111; 523/118; 524/297; 422/1; 422/22; 514/527
[58] Field of Search ................................ 522/74, 79, 173, 522/1, 152; 523/111, 118; 514/527; 422/1, 22; 524/292

[56] References Cited

U.S. PATENT DOCUMENTS

| | | | |
|---|---|---|---|
| 2,721,858 | 10/1955 | Joyner et al. | 260/67 |
| 2,904,392 | 9/1959 | Pomerantz et al. | 21/54 |
| 2,921,006 | 1/1960 | Schmitz et al. | 204/154 |
| 3,122,633 | 2/1964 | Steigerwald | 250/49.5 |
| 3,254,111 | 5/1966 | Hawkins et al. | |
| 3,554,990 | 1/1971 | Quinn et al. | 428/522 |
| 3,704,089 | 11/1972 | Stehlik et al. | 422/22 |
| 3,780,308 | 12/1973 | Nablo | 250/492 |
| 3,940,362 | 2/1976 | Overhults | 523/116 |
| 3,995,641 | 12/1976 | Kronenthal et al. | 606/214 |
| 4,127,382 | 11/1978 | Perry | 8/181 |
| 4,364,876 | 12/1982 | Kimura et al. | 558/443 |
| 5,259,835 | 11/1993 | Clark et al. | 602/48 |
| 5,328,687 | 7/1994 | Leung et al. | 424/78.35 |
| 5,514,371 | 5/1996 | Leung et al. | 424/78.35 |
| 5,514,372 | 5/1996 | Leung et al. | 424/78.35 |
| 5,530,037 | 6/1996 | McDonnell et al. | 522/79 |
| 5,575,997 | 11/1996 | Leung et al. | 424/78.35 |
| 5,582,834 | 12/1996 | Leung et al. | 424/78.35 |
| 5,624,669 | 4/1997 | Leung et al. | 424/78.35 |
| 5,753,699 | 5/1998 | Greff et al. | |
| 5,874,044 | 2/1999 | Kotzev | |
| 5,998,472 | 12/1999 | Berger et al. | |

FOREIGN PATENT DOCUMENTS

| | | |
|---|---|---|
| WO 99/18950 | 4/1999 | WIPO . |
| WO 00/16615 | 3/2000 | WIPO . |

*Primary Examiner*—James J. Seidleck
*Assistant Examiner*—Sanza McClendon
*Attorney, Agent, or Firm*—Oliff & Berridge, PLC

[57] ABSTRACT

A method for sterilizing a liquid adhesive composition includes subjecting the composition to electron beam irradiation while it is enclosed in a container.

26 Claims, No Drawings

ELECTRON BEAM STERILIZATION OF LIQUID ADHESIVE COMPOSITIONS

BACKGROUND OF THE INVENTION

1. Field of Invention

The present invention is directed to treatment of liquid compositions that are useful as biomedical adhesives and sealants, particularly methods of sterilizing them. More particularly, the present invention relates to a method using electron beam irradiation to sterilize monomeric liquid adhesive compositions, for example 1,1-disubstituted ethylene monomers.

2. Description of Related Art

Several methods are known for sterilizing monomeric and polymeric compositions.

U.S. Pat. No. 5,530,037 to McDonnell et al. discloses sterilizing cyanoacrylates using gamma radiation. Additionally, several other methods are disclosed including ionizing radiation. However, most of these methods are said to be unsuitable in their applicability to cyanoacrylate adhesives. In particular, the '037 patent states that electron beam accelerators have relatively low penetration and are effective only in sterilizing the outer surface of a container.

U.S. Pat. No. 2,904,392 to Pomerantz et al. discloses a method of packaging various chemicals, gasoline, polymerized plastics, or polymerizable monomers in film-formed bags and subjecting the bags to high intensity ionizing irradiation to effect sterilization. The radiation is obtainable from beams of high energy electrons produced by high voltage electron accelerators. In the case of monomers, irradiation at a suitable dosage level can be utilized to initiate polymerization without the assistance of a chemical catalyst or promoter. In this manner, polymerization can be achieved at low temperatures and the resultant polymer is essentially pure.

U.S. Pat. No. 3,704,089 to Stehlik discloses a process for the sterilization of monomeric esters of α-cyanoacrylic acids. The sterilization is carried out by ionizing irradiation (e.g., Co 60-gamma irradiation) after the esters have cooled, preferably to below their solidification points.

U.S. Pat. No. 2,921,006 to Schmitz et al. discloses polymerization of organic compounds with high energy electrons and, more particularly, polymerization of such compounds in the liquid or solid state by irradiation with high energy electrons. The organic compounds are contained in a receptacle covered with an aluminum sheet.

U.S. Pat. No. 3,122,633 to Steigerwald discloses an apparatus for polymerization of liquid materials by subdividing a polymer organic material into small volumes and irradiating the material while in the subdivided state with an electron beam source.

U.S. Pat. No. 3,780,308 to Nablo discloses surface sterilization and/or surface treatment of containers and other articles, the walls of which have a high specific energy absorption for relatively low energy electrons. The electron beam slightly penetrates container walls to effect surface sterilization, while substantially absorbing the electrons within the walls to minimize x-ray generation.

SUMMARY OF THE INVENTION

The present invention is directed to methods for sterilizing a liquid adhesive composition, preferably a monomeric composition, in a container using electron beam irradiation. The liquid adhesive composition of the present invention may comprise a 1,1-disubstituted ethylene monomer.

The present invention uses electron beam irradiation to sterilize liquid adhesive compositions inside their containers. In preferred embodiments, there is substantially no initiation of polymerization of monomeric liquid adhesive compositions that affects the utility of the monomer or monomers. Benefits of electron beam irradiation include the ability to sterilize the liquid composition on a production line without initiating any substantial polymerization, in a few seconds and at a lower penetration than gamma irradiation. The sterilized liquid adhesive compositions have good shelf life and excellent stability. The temperature levels of the liquid adhesive compositions during electron beam irradiation change only slightly from room temperature. In addition, post sterilization microbiological testing and a quarantine period are not required.

DETAILED DESCRIPTION OF PREFERRED EMBODIMENTS

The present invention is directed to sterilizing a liquid adhesive composition in a container using electron beam irradiation. In embodiments, the liquid adhesive composition is subjected to a dosage of about 0.5–10 MRad (5–100 kGy), preferably about 1.0–5.0 MRad (10–50 kGy), and more preferably 2–3 Mrad (20–30 kGy), of electron beam irradiation. The time of exposure is relative to the strength of the beam and is typically in the range of tenths of a second to seconds (depending on the conveyor speed) and is preferably less than one minute. Time of exposure will change from day to day depending on the beam strength at the time of setup. Dosimeters may be used to determine the exposure of the samples.

There are several sources for electron beam irradiation. The two main groups of electron beam accelerators are: (1) a Dynamitron, which uses an insulated core transformer, and (2) radio frequency (RF) linear accelerators (linacs). The Dynamitron is a particle accelerator (4.5 MeV) designed to impart energy to electrons. The high energy electrons are generated and accelerated by the electrostatic fields of the accelerator electrodes arranged within the length of the glass-insulated beam tube (acceleration tube). These electrons, traveling through an extension of the evacuation beam tube and beam transport (drift pipe) are subjected to a magnet deflection system in order to produce a "scanned" beam, prior to leaving the vacuum enclosure through a beam window. The dose can be adjusted with the control of the percent scan, the beam current and the conveyor speed.

The liquid adhesive composition may be in any type of at least partially electron beam permeable container, including, but not limited to, glass, plastic, and film-formed packages. In embodiments of the present invention, the container may be sealed or have an opening. Examples of glass containers include, but are not limited to, ampules, vials, syringes, pipettes, applicators, and the like. The penetration of electron beam irradiation is a function of the packaging. If there is not enough penetration from the side of a stationary electron beam, the container may be flipped or rotated to achieve adequate penetration. Alternatively, the electron beam source can be moved about a stationary package. In order to determine the dose distribution and dose penetration in product load, a dose map can be performed. This will identify the minimum and maximum dose zone within a product.

In embodiments, after the container containing the liquid adhesive composition is sterilized with electron beam irradiation, the container may be subjected to gamma irradiation. For example, the container may be placed in a kit with other components that need to be sterilized. The entire kit may then be sterilized. In addition to gamma irradiation, the entire kit may be sterilized by chemical (e.g., with ethylene oxide or hydrogen peroxide vapor), physical (e.g., dry heat) or other techniques such as microwave irradiation and electron beam irradiation.

The liquid composition in embodiments is preferably a monomeric adhesive composition. In embodiments, the monomer is a 1,1-disubstituted ethylene monomer, e.g., an alpha-cyanoacrylate. Preferred monomer compositions of the present invention and polymers formed therefrom are useful as tissue adhesives, sealants for preventing bleeding or for covering open wounds, and in other biomedical applications. They find uses in, for example, apposing surgically incised or traumatically lacerated tissues; retarding blood flow from wounds; drug delivery; dressing burns; and aiding repair and regrowth of living tissue.

Conventional surgical adhesive compositions have included plasticizers with the adverse effect of reducing the film strength. It has been discovered that, contrary to prior belief, the film strength (e.g., toughness) under certain conditions is not adversely reduced upon the addition of greater amounts of plasticizing agent. Depending on the particular acidic stabilizing agent and the purity of the monomer utilized in the adhesive composition, the addition of greater amounts of plasticizing agent may increase the toughness of the resulting bond formed on the wound. Acidic stabilizing agents do not significantly affect the polymerization of the monomer in the present composition and provide increased film strength with increasing amounts of plasticizing agents.

Monomers that may be used in this invention are readily polymerizable, e.g. anionically polymerizable or free radical polymerizable, to form polymers. Such monomers include those that form polymers, which may, but do not need to, biodegrade. Reference is made, for example, to U.S. Pat. No. 5,328,687, which is hereby incorporated by reference herein. As defined herein, "histotoxicity" refers to adverse tissue response, such as inflammation due to the presence of toxic materials in the tissue.

Useful 1,1-disubstituted ethylene monomers include, but are not limited to, monomers of the formula:

$$HRC=CXY \quad (I)$$

wherein X and Y are each strong electron withdrawing groups, and R is H, —CH=CH$_2$ or, provided that X and Y are both cyano groups, a C$_1$–C$_4$ alkyl group.

Examples of monomers within the scope of formula (1) include alpha-cyanoacrylates, vinylidene cyanides, C$_1$–C$_4$ alkyl homologues of vinylidene cyanides, dialkyl methylene malonates, acylacrylonitriles, vinyl sulfinates and vinyl sulfonates of the formula CH$_2$=CX'Y wherein X' is —SO$_2$R' or —SO$_3$R' and Y' is —CN, —COOR', —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula

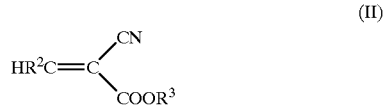

(II)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2–4 carbon atoms, R$^5$ is an alkylene group having 2–4 carbon atoms, and R$^6$ is an alkyl group having 1–6 carbon atoms; or a group having the formula

, wherein R$^7$ is

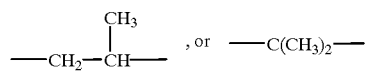 , or 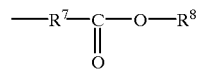

wherein n is 1–10, preferably 1–5 carbon atoms and R$^8$ is an organic moiety.

Examples of suitable hydrocarbyl and substituted hydrocarbyl groups include straight chain or branched chain alkyl groups having 1–16 carbon atoms; straight chain or branched chain C$_1$–C$_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety R$^8$ may be substituted or unsubstituted and may be straight chain, branched or cyclic, saturated, unsaturated or aromatic. Examples of such organic moieties include C$_1$–C$_8$ alkyl moieties, C$_2$–C$_8$ alkenyl moieties, C$_2$–C$_8$ alkynyl moieties, C$_3$–C$_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 6 carbon atoms.

In the cyanoacrylate monomer of formula (II), R$^3$ is preferably an alkyl group having 1–10 carbon atoms or a group having the formula —AOR$^9$, wherein A is a divalent straight or branched chain alkylene or oxyalkylene moiety having 2–8 carbon atoms, and R$^9$ is a straight or branched alkyl moiety having 1–8 carbon atoms.

Examples of groups represented by the formula —AOR$^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

The alpha-cyanoacrylates of formula (II) can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a nonaqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (II) wherein $R^3$ is a group having the formula —$R^4$—O—$R^5$—O—$R^6$ can be prepared according to the method disclosed in U.S. Pat. No. 4,364,876 to Kimura et al., which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (II) wherein $R^3$ is a group having the formula

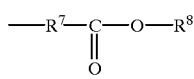

can be prepared according to the procedure described in U.S. Pat. No. 3,995,641 to Kronenthal et al., which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (II) include cyanopentadienoates and alpha-cyanoacrylates of the formula:

(III)

wherein Z is —CH=$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated by reference herein.

Preferred monomers are alkyl alpha-cyanoacrylates and more preferably octyl alpha-cyanoacrylates, especially 2-octyl alpha-cyanoacrylate. Monomers utilized in the present application should be very pure and contain few impurities (e.g., surgical grade).

The compositions of the present invention may include at least one plasticizing agent that imparts flexibility to the polymerized monomer formed on the wound or incision. The plasticizing agent preferably contains little or no moisture and should not significantly affect the polymerization of the monomer.

Other compositions are exemplified by U.S. Pat. Nos. 5,259,835 and 5,328,687 and U.S. patent application Ser. Nos. 08/609,921, 08/714,288, 08/909,845, 08/755,007, 08/920,876, and 08/488,411, all incorporated by reference herein in their entirety.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The compositions of the present invention may also include at least one acidic stabilizing agent that inhibits polymerization. Such stabilizing agents may also include mixtures of anionic stabilizing agents and radical stabilizing agents.

Examples of suitable anionic stabilizing agents include, but are not limited to, sultones (e.g., α-chloro-α-hydroxy-o-toluenesulfonic acid-γ-sultone), sulfur dioxide, sulfuric acid, sulfonic acid, lactone, boron trifluoride, organic acids, such as acetic acid or phosphoric acid, alkyl sulfate, alkyl sulfite, 3-sulfolene, alkylsulfone, alkyl sulfoxide, mercaptan, and alkyl sulfide and mixtures thereof. Preferable anionic stabilizing agents are acidic stabilizing agents of organic acids such as acetic acid or phosphoric acid. In embodiments, the amount of sulfur dioxide stabilizer is less than 100 ppm, preferably 5–75 ppm, and more preferably from about 20–50 ppm. The amount of sultone and/or trifluoracetic acid is about 500–3000 ppm.

Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole (BHA), butylated hydroxy toluene, and t-butyl hydroquinone. In embodiments, the amount of BHA is about 1,000–5,000 ppm.

Suitable acidic stabilizing agents include those having aqueous $pK_a$ ionization constants ranging from −12 to 7, about −5 to about 7, preferably from about −3.5 to about 6, and more preferably from about 2 to about 5.5. For example, suitable acidic stabilizing agents include: hydrogen sulfide ($pK_a$ 7.0), carbonic acid ($pK_a$ 6.4), triacetylmethane ($pK_a$ 5.9), acetic acid ($pK_a$ 4.8), benzoic acid ($pK_a$ 4.2), 2,4-dinitrophenol ($pK_a$ 4.0), formic acid ($pK_a$ 3.7), nitrous acid ($pK_a$ 3.3), hydrofluoric acid ($pK_a$ 3.2), chloroacetic acid ($pK_a$ 2.9), phosphoric acid ($pK_a$ 2.2), dichloroacetic acid ($pK_a$ 1.3), trichloroacetic acid ($pK_a$ 0.7), 2,4,6-trinitrophenol (picric acid) ($pK_a$ 0.3), trifluoroacetic acid ($pK_a$ 0.2), sulfuric acid ($pK_a$ −3.0) and mixtures thereof. In embodiments, the amount of trifluoroacetic acid is about 500–1,500 ppm.

When adding the above-mentioned acidic stabilizing agents to the adhesive composition, the addition of plasticizing agents in amounts ranging from about 0.5 wt. % to about 16 wt. %, preferably from about 3 wt. % to about 9 wt. %, and more preferably from about 5 wt. % to about 7 wt. % provides increased film strength (e.g., toughness) of the polymerized monomer over polymerized monomers having amounts of plasticizing agents and acidic stabilizing agents outside of the above ranges.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid such as phosphoric acid, a concentration range of 20–80 ppm (wt/wt), preferably, 30–70 ppm (wt/wt) and more preferably 40–60 ppm (wt/wt) may be utilized. In embodiments, the amount of trifluoroacetic acid is about 100 to 3000 ppm, preferably 500–1500 ppm. In other embodiments, the amount of phosphoric acid is about 10–200 ppm, preferably about 50–150 ppm, and more preferably about 75–125 ppm.

Other compositions are exemplified by U.S. Pat. Nos. 5,624,669, 5,582,834, 5,575,997, 5,514,371, 5,514,372, 5,259,835 and 5,328,687, incorporated by reference herein in their entirety. The compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soybean protein, vegetable protein, keratin and glue. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated by reference herein. Such heterocyclic compounds include, for example, benzimidazole, 5-methyl benzimidazole, 2-methylbenzimidazole, indole, pyrrole, 1,2, 4-triazole, indoline, benzotriazole, indoline, and the like.

A preferred formaldehyde scavenger for use in this invention is sodium bisulfite.

In practicing the present invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. Other compositions are exemplified by U.S. patent application Ser. No. 08/714,288, incorporated by reference herein in their entirety.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such "bioerosion" can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of the surfactant which can be added to the mineral oil include those commercially available under the designations Triton x-100, Tween 20 and Tween 80.

The composition of this invention may further contain one or more adjuvant substances, such as thickening agents, medicaments, or the like, to improve the medical utility of the monomer for particular medical applications.

Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions of this invention, difunctional monomeric cross-linking agents may be added to the monomer compositions of this invention. Such crosslinking agents are known. Reference is made, for example, to U.S. Pat. No. 3,940,362 to Overhults, which is hereby incorporated by reference herein. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymerization or to modify the rate of polymerization of the cyanoacrylate monomer/crosslinking agent blend.

In embodiments, the adhesive compositions may additionally contain heat and/or light (e.g., visible or ultraviolet light) activated initiators and accelerators that initiate crosslinking of cyanoacrylate compositions containing compounds of formula (I).

Particular initiators for particular systems may be readily selected by one of ordinary skill in the art without undue experimentation. Suitable polymerization initiators for the cyanoacrylate compositions include, but are not limited to, detergent compositions; surfactants: e.g., nonionic surfactants such as polysorbate 20 (e.g., Tween 20™), polysorbate 80 (e.g., Tween 80™) and poloxamers, cationic surfactants such as tetrabutylammonium bromide, anionic surfactants such as benzalkonium chloride or its pure components, stannous octoate (tin (II) 2-ethylheaxanoate), and sodium tetradecyl sulfate, and amphoteric or zwitterionic surfactants such as dodecyldimethyl(3-sulfopropyl)ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; and organometallics and manganese acetylacetonate and radical initiators. Cobalt naphthenate can be used as an accelerator for peroxide.

The compositions of the present invention may further contain fibrous reinforcement and colorants, i.e., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9, 10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphenyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Depending on the particular requirements of the user, the liquid compositions of the present invention can be applied by known means such as with a glass stirring rod, sterile brush or medicine dropper. However, in many situations a pressurized aerosol dispensing package is preferred in which the adhesive composition is in solution with a compatible anhydrous propellant.

EXAMPLES

The following Examples illustrate specific embodiments of the invention. These examples are intended to be illustrative only, and the invention is not limited to the materials, conditions or process parameters set forth in the Examples.

Table 1 shows the stabilizer concentrations for runs 1–20 in Tables 2–7. Table 8 shows the stabilizer concentrations for runs 1–27 in Tables 9–11.

Tables 2 and 5 show the initial viscosity for 2-octylcyanoacrylate monomeric compositions containing less than 5 ppm SO2 and without $SO_2$ respectively when sterilized by electron beam irradiation. Tables 3–4 show the change in viscosity over time (d=days) for 2-octylcyanoacrylate compositions containing less than 5 ppm $SO_2$ that have been sterilized by electron beam irradiation. Tables 6–7 show the change in viscosity over time for 2-octylcyanoacrylate compositions containing no $SO_2$ that have been sterilized by electron beam irradiation. The change in viscosity is a measure of polymerization and thus the stability of the liquid adhesive monomeric compositions.

Table 9 shows the initial viscosity for 2-octylcyanoacrylate monomeric compositions containing 1500 ppm hydroquinone and 27 ppm $SO_2$ when sterilized by electron beam irradiation. Tables 10–11 demonstrate that monomeric compositions containing stabilizing agents exhibit good stability as shown by the small change in containing stabilizing agents exhibit good stability as shown by the small change in viscosity when sterilized by electron beam irradiation. Table 12 demonstrates that n-butyl cyanoacrylate monomeric compositions also exhibit good stability when sterilized by electron beam irradiation.

In the Accelerated Stability Results conducted at 80° C. to analyze stability and self-life, 3 days at 80° C. is approximately 6 months at room temperature, 6 days at 80° C. is approximately 1 year at room temperature and 12 days at 80° C. is approximately 2 years at room temperature. N.D. means no data. Viscosity is measured at 25° C.

TABLE 1

Stabilizer Concentrations

| Run | Sultone (ppm) | BHA (ppm) | TFA (ppm) |
|---|---|---|---|
| 1 | 1000 | 3000 | 1500 |
| 2 | 1500 | 5000 | 500 |
| 3 | 500 | 5000 | 500 |
| 4 | 1000 | 1000 | 1000 |
| 5 | 1000 | 5000 | 1000 |
| 6 | 500 | 5000 | 1500 |
| 7 | 500 | 3000 | 1000 |
| 8 | 1000 | 3000 | 1000 |
| 9 | 1500 | 1000 | 500 |
| 10 | 1000 | 3000 | 500 |
| 11 | 1000 | 3000 | 1000 |
| 12 | 1000 | 3000 | 1000 |
| 13 | 500 | 1000 | 500 |
| 14 | 1000 | 3000 | 1000 |
| 15 | 1500 | 3000 | 1000 |
| 16 | 1000 | 3000 | 1000 |
| 17 | 1500 | 5000 | 1500 |
| 18 | 1500 | 1000 | 1500 |
| 19 | 1000 | 3000 | 1000 |
| 20 | 500 | 1000 | 1500 |

TABLE 2

2OCA Formulations with SO2
Viscosity (cps)

| Run | Control | 20 kGy | 30 kGy |
|---|---|---|---|
| 1 | 6.1 | 7.8 | 9.5 |
| 2 | 6.2 | 7.6 | 9.2 |
| 3 | 6.3 | 7.0 | 8.4 |
| 4 | 6.2 | 7.1 | 7.9 |
| 5 | 6.3 | 6.8 | 7.9 |
| 6 | 6.3 | 7.7 | 9.9 |
| 7 | 6.4 | 7.3 | N.D. |
| 8 | 6.3 | 7.1 | 8.4 |
| 9 | 6.3 | 7.1 | 8.4 |
| 10 | 6.2 | 7.1 | 8.5 |
| 11 | 6.2 | 7.3 | 8.5 |
| 12 | 6.2 | 7.1 | 8.5 |
| 13 | 6.3 | 7.2 | 8.5 |
| 14 | 6.2 | 7.2 | 8.6 |
| 15 | 6.1 | 6.9 | 8.3 |
| 16 | 6.1 | 7.8 | 10.2 |
| 17 | 6.1 | 7.6 | 9.3 |
| 18 | 6.1 | 7.1 | 8.3 |
| 19 | 6.2 | 7.1 | 8.2 |
| 20 | 6.3 | 6.9 | 7.8 |

TABLE 3

2OCA Formulations with SO2
20 kGy Exposed Samples
Accelerated Stability Results (80° C.)
Viscosity (cps)

| Run | t = 0 | t = 6 d | t = 12 d |
|---|---|---|---|
| 1 | 7.8 | 30 | 449 |
| 2 | 7.6 | 1000 | 1000 |
| 3 | 7.0 | 69 | N.D. |
| 4 | 7.1 | 25 | 401 |
| 5 | 6.8 | 1000 | 1000 |
| 6 | 7.7 | 28 | 1000 |
| 7 | 7.3 | 15 | N.D. |
| 8 | 7.1 | 54 | 1000 |
| 9 | 7.1 | 23 | 1000 |
| 10 | 7.1 | 37 | 1000 |
| 11 | 7.3 | 33 | 1000 |
| 12 | 7.1 | 53 | 1000 |
| 13 | 7.2 | 45 | 1000 |
| 14 | 7.2 | 23 | 1000 |
| 15 | 6.9 | 20 | 478 |
| 16 | 7.8 | 20 | 177 |
| 17 | 7.6 | 50 | 1000 |
| 18 | 7.1 | 22 | 1000 |
| 19 | 7.1 | 16 | 304 |
| 20 | 6.9 | 34 | 1000 |

TABLE 4

2OCA Formulations with SO2
30 kGy Exposed Samples
Accelerated Stability Results (80° C.)
Viscosity (cps)

| Run | Control | t = 6 d | t = 12 d |
|---|---|---|---|
| 1 | 9.5 | 191 | 1000 |
| 2 | 9.2 | 1000 | 1000 |
| 3 | 8.4 | 540 | 1000 |
| 4 | 7.9 | 384 | 1000 |
| 5 | 7.9 | 1000 | 1000 |
| 6 | 9.9 | 97 | 1000 |
| 7 | N.D. | N.D. | N.D. |
| 8 | 8.4 | 242 | 1000 |
| 9 | 8.4 | 63 | 1000 |
| 10 | 8.5 | 111 | 1000 |
| 11 | 8.5 | 130 | 1000 |
| 12 | 8.5 | 552 | 1000 |
| 13 | 8.5 | 157 | 1000 |
| 14 | 8.6 | 63 | 1000 |
| 15 | 8.3 | 49 | 1000 |
| 16 | 10.2 | 59 | 1000 |
| 17 | 9.3 | 187 | 1000 |
| 18 | 8.3 | 50 | 1000 |
| 19 | 8.2 | 26 | 1000 |
| 20 | 7.8 | 87 | 1000 |

TABLE 5

2OCA Formulations without SO2
Viscosity (cps)

| Run | Control | 20 kGy | 30 kGy |
|---|---|---|---|
| 1 | 6.1 | 8.2 | 9.8 |
| 2 | 6.2 | 7.9 | 9.1 |
| 3 | 6.2 | 7.5 | 8.3 |
| 4 | 6.1 | 7.2 | 7.9 |
| 5 | 6.1 | 6.6 | 7.8 |
| 6 | 6.3 | 7.8 | 9.6 |
| 7 | 6.1 | 7.4 | 8.1 |
| 8 | 6.1 | 7.3 | 8.0 |
| 9 | 6.1 | 7.4 | 8.3 |
| 10 | 6.2 | 7.5 | 8.3 |
| 11 | 6.1 | 7.5 | 8.2 |
| 12 | 6.3 | 7.4 | 8.2 |
| 13 | 6.0 | 7.3 | 8.3 |
| 14 | 6.2 | 7.5 | 8.1 |
| 15 | 6.2 | 7.3 | 7.8 |
| 16 | 6.0 | 8.6 | 10.7 |
| 17 | 6.1 | 8.6 | 11.0 |
| 18 | 6.1 | 7.7 | 8.6 |
| 19 | 6.1 | 7.4 | 8.0 |
| 20 | 6.2 | 7.2 | 7.5 |

TABLE 6

2OCA Formulations without SO2
20 kGy Exposed Samples
Accelerated Stability Results (80° C.)
Viscosity (cps)

| Run | Control | t = 6 d | t = 12 d |
|---|---|---|---|
| 1 | 8.2 | 1000 | 1000 |
| 2 | 7.9 | 1000 | 1000 |
| 3 | 7.5 | 1000 | 1000 |
| 4 | 7.2 | 1000 | 1000 |
| 5 | 6.6 | 1000 | 1000 |
| 6 | 7.8 | 1000 | 1000 |
| 7 | 7.4 | 329 | 1000 |
| 8 | 7.3 | 1000 | 1000 |
| 9 | 7.4 | 345 | 1000 |
| 10 | 7.5 | 262 | 1000 |
| 11 | 7.5 | 520 | 1000 |
| 12 | 7.4 | 417 | 1000 |
| 13 | 7.3 | 198 | 1000 |
| 14 | 7.5 | 213 | 1000 |
| 15 | 7.3 | 428 | 1000 |
| 16 | 8.6 | 1000 | 1000 |
| 17 | 8.6 | 1000 | 1000 |
| 18 | 7.7 | 20 | N.D. |
| 19 | 7.4 | 16 | 92.0 |
| 20 | 7.2 | 37 | N.D. |

TABLE 7

2OCA Formulations without SO2
30 kGy Exposed Samples
Accelerated Stability results (80° C.)
Viscosity (cps)

| Run | Control | t = 6 d | t = 12 d |
|---|---|---|---|
| 1 | 9.8 | 1000 | 1000 |
| 2 | 9.1 | 1000 | 1000 |
| 3 | 8.3 | 1000 | 1000 |
| 4 | 7.9 | 1000 | 1000 |
| 5 | 7.8 | 1000 | 1000 |
| 6 | 9.6 | 1000 | 1000 |
| 7 | 8.1 | 1000 | 1000 |
| 8 | 8.0 | 1000 | 1000 |
| 9 | 8.3 | 1000 | 1000 |
| 10 | 8.3 | 1000 | 1000 |
| 11 | 8.2 | 1000 | 1000 |
| 12 | 8.2 | 1000 | 1000 |
| 13 | 8.3 | 1000 | 1000 |
| 14 | 8.1 | 1000 | 1000 |
| 15 | 7.8 | 1000 | 1000 |
| 16 | 10.7 | 1000 | 1000 |
| 17 | 11.0 | 1000 | 1000 |
| 18 | 8.6 | 1000 | 1000 |
| 19 | 8.0 | 149 | 1000 |
| 20 | 7.5 | 240 | 1000 |

TABLE 8

Stabilizer Concentrations

| Run | Sultone (ppm) | BHA (ppm) | TFA (ppm) |
|---|---|---|---|
| 1 | 0 | 500 | 0 |
| 2 | 0 | 500 | 750 |
| 3 | 0 | 500 | 1500 |
| 4 | 0 | 2000 | 0 |
| 5 | 0 | 2000 | 750 |
| 6 | 0 | 2000 | 1500 |
| 7 | 0 | 3500 | 0 |
| 8 | 0 | 3500 | 750 |
| 9 | 0 | 3500 | 1500 |
| 10 | 750 | 500 | 0 |
| 11 | 750 | 500 | 750 |
| 12 | 750 | 500 | 1500 |
| 13 | 750 | 2000 | 0 |
| 14 | 750 | 2000 | 750 |
| 15 | 750 | 2000 | 1500 |
| 16 | 750 | 3500 | 0 |
| 17 | 750 | 3500 | 750 |
| 18 | 750 | 3500 | 1500 |
| 19 | 1500 | 500 | 0 |
| 20 | 1500 | 500 | 750 |
| 21 | 1500 | 500 | 1500 |
| 22 | 1500 | 2000 | 0 |
| 23 | 1500 | 2000 | 750 |
| 24 | 1500 | 2000 | 1500 |
| 25 | 1500 | 3500 | 0 |
| 26 | 1500 | 3500 | 750 |
| 27 | 1500 | 3500 | 1500 |

TABLE 9

Initial Results (t = 0)
Viscosity (cps)

| Run | Control | 20 kGy | 30 kGy |
|---|---|---|---|
| 1 | 6.8 | 10.2 | 12.0 |
| 2 | 6.6 | 8.6 | 9.8 |
| 3 | 6.7 | 8.7 | 10.0 |
| 4 | 6.7 | 9.4 | 11.0 |
| 5 | 6.7 | 8.3 | 9.3 |
| 6 | 6.7 | 8.1 | 8.7 |
| 7 | 6.6 | 9.1 | 10.0 |
| 8 | 6.6 | 8.5 | 8.9 |
| 9 | 6.6 | 8.6 | 8.4 |
| 10 | 6.6 | 10.3 | 12.0 |
| 11 | 6.7 | 9.3 | 10.0 |
| 12 | 6.6 | 9.1 | 9.5 |
| 13 | 6.8 | 9.8 | 11.0 |
| 14 | 6.7 | 8.9 | 9.3 |
| 15 | 6.7 | 8.6 | 9.2 |
| 16 | 6.6 | 9.4 | 9.7 |
| 17 | 6.8 | 8.6 | 9.6 |
| 18 | 6.8 | 8.5 | 9.3 |
| 19 | 6.8 | 10.0 | 11.0 |
| 20 | 6.5 | 9.7 | 11.2 |
| 21 | 6.7 | 9.2 | 10.7 |
| 22 | 6.7 | 9.7 | 11.0 |
| 23 | 6.8 | 9.0 | 9.8 |
| 24 | 6.9 | 8.6 | 9.8 |
| 25 | 6.7 | 9.3 | 10.0 |
| 26 | 6.7 | 8.8 | 9.8 |
| 27 | 6.6 | 8.6 | 8.8 |

TABLE 10

20 kGy Exposed
Accelerated Stability Results (80° C.)
Viscosity (cps)

| Run | t = 0 | t = 3d |
|---|---|---|
| 1 | 10.2 | 13 |
| 2 | 8.6 | 14 |
| 3 | 8.7 | 16 |
| 4 | 9.4 | 11 |
| 5 | 8.3 | 11 |
| 6 | 8.1 | 16 |
| 7 | 9.1 | 11 |
| 8 | 8.5 | 11 |
| 9 | 8.6 | 13 |

TABLE 10-continued 20 kGy Exposed
Accelerated Stability Results (80° C.)
Viscosity (cps)

| Run | t = 0 | t = 3d |
|---|---|---|
| 10 | 10.3 | 12 |
| 11 | 9.3 | 13 |
| 12 | 9.1 | 15 |
| 13 | 9.8 | 11 |
| 14 | 8.9 | 11 |
| 15 | 8.6 | 14 |
| 16 | 9.4 | 11 |
| 17 | 8.6 | 11 |
| 18 | 8.5 | 12 |
| 19 | 10.0 | 13 |
| 20 | 9.7 | 13 |
| 21 | 9.2 | 14 |
| 22 | 9.7 | 12 |
| 23 | 9.0 | 11 |
| 24 | 8.6 | 12 |
| 25 | 9.3 | 11 |
| 26 | 8.8 | 11 |
| 27 | 8.6 | 13 |

TABLE 11

30 kGy Exposed
Accelerated Stability Results (80° C.)
Viscosity (cps)

| Run | t = 0 | t = 3d |
|---|---|---|
| 1 | 12.0 | 21 |
| 2 | 9.8 | 23 |
| 3 | 10.0 | 24 |
| 4 | 11.0 | 18 |
| 5 | 9.3 | 18 |
| 6 | 8.7 | 22 |
| 7 | 10.0 | 15 |
| 8 | 8.9 | 15 |
| 9 | 8.4 | 18 |
| 10 | 12.0 | 18 |
| 11 | 10.0 | 16 |
| 12 | 9.5 | 19 |
| 13 | 11.0 | 14 |
| 14 | 9.3 | 13 |
| 15 | 9.2 | 17 |
| 16 | 9.7 | 13 |
| 17 | 9.6 | 14 |
| 18 | 9.3 | 15 |
| 19 | 11.0 | 16 |
| 20 | 11.2 | 17 |
| 21 | 10.7 | 18 |
| 22 | 11.0 | 15 |
| 23 | 9.8 | 15 |
| 24 | 9.8 | 16 |
| 25 | 10.0 | 14 |
| 26 | 9.8 | 13 |
| 27 | 8.8 | 14 |

TABLE 12

| Weeks at 50° C. | Viscosity (cps) | | | | | |
|---|---|---|---|---|---|---|
| | 0 kGy | 10 kGy | 20 kGy | 30 kGy | 40 kGy | 50 kGy |
| 0 | 3.0 | 4.1 | 5.0 | 8.9 | 22 | 153 |
| 1 | 3.1 | 4.2 | 5.0 | 9.4 | 24 | 375 |
| 4 | 3.2 | 4.2 | 7.7 | 8.8 | 1000 | 1000 |
| 8 | 3.0 | 5.5 | 15 | 129 | 1000 | 1000 |
| 12 | 3.5 | 8.7 | 119 | 1000 | 1000 | 1000 |
| 14 | 3.4 | 12 | 695 | 1000 | 1000 | 1000 |

What is claimed is:

1. A method for sterilizing a liquid monomeric adhesive composition, comprising:

placing said composition into a container, and
subjecting said container to electron beam irradiation at a dose sufficient to sterilize said composition,
wherein said subjecting step causes substantially no initiation of polymerization of the liquid adhesive composition and said sterilization is sufficient to render said composition suitably sterile for application to open wounds.

2. The method according to claim 1, wherein said composition comprises a 1,1-disubstituted ethylene monomer.

3. The method according to claim 2, wherein said monomer is octylcyanoacrylate or butylcyanoacrylate.

4. The method according to claim 1, wherein said container is sealed.

5. The method according to claim 1, wherein said container is at least partially electron beam permeable.

6. The method according to claim 1, wherein said container is made of glass.

7. The method according to claim 1, wherein said container is made of plastic.

8. The method according to claim 6, wherein said container is selected from the group consisting of ampules, vials, syringes, pipettes, tubes and applicators.

9. The method according to claim 1, wherein said electron beam irradiation has a dosage of from about 0.5–10.0 MRad.

10. The method according to claim 1, wherein said electron beam irradiation has a dosage of from about 1.5–5.0 MRad.

11. The method according to claim 1, wherein said dosage is from about 2.0–3.0 MRad.

12. The method according to claim 1, wherein said subjecting to electron beam irradiation lasts for less than 1 minute.

13. The method according to claim 1, further comprising subjecting said container to chemical, physical or irradiation sterilization.

14. The method according to claim 1, further comprising subjecting said container to gamma irradiation, microwave irradiation, ethylene oxide, hydrogen peroxide vapor or dry heat.

15. The method according to claim 1, wherein said composition further comprises a stabilizing agent having an aqueous $pK_a$ of −12 to 7.

16. The method according to claim 15, wherein said stabilizing agent is selected from the group consisting of sulfur dioxide, sulfuric acid, trifluroacetic acid, butylated hydroxy anisole, butylated hydroxy toulene, hydroquinone and sultone.

17. The method according to claim 15, wherein said stabilizing agent is butylated hydroxy anisole.

18. The method according to claim 15, wherein said stabilizing agent is sulfuric acid.

19. The method according to claim 16, wherein said sulfur dioxide is present in an amount of less than about 27 ppm.

20. The method according to claim 15, wherein said stabilizing agent is hydroquinone.

21. The method according to claim 1, wherein said composition further comprises a thickening agent.

22. The method according to claim 21, wherein said thickening agent is selected from the group consisting of polyalkyl acrylates, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

23. The method according to claim 1, wherein said composition comprises a mixture of anionic stabilizing agents and radical stabilizing agents.

24. The method according to claim 23, wherein said mixture comprises sulfur dioxide, sulfuric acid, butylated hydroxy anisole (BHA).

25. The method according to claim 23, wherein said mixture comprises sulfur dioxide, sulfuric acid, butylated hydroxy anisole (BHA), and hydroquinone.

26. The method according to claim 1, wherein said composition comprises an $\alpha$-cyanoacrylate monomer.

* * * * *